United States Patent [19]

Beltz et al.

[11] Patent Number: 5,073,552
[45] Date of Patent: Dec. 17, 1991

[54] SUBSTITUTED BENZOPHENONE DICARBOXYLIC ACIDS

[75] Inventors: Mark W. Beltz; Venkataraman Ramachandran, both of Baton Rouge, La.

[73] Assignee: Ethyl Corporation, Richmond, Va.

[21] Appl. No.: 576,849

[22] Filed: Sep. 4, 1990

[51] Int. Cl.$^5$ ............................................. C07D 305/00
[52] U.S. Cl. .................................... 549/214; 549/468; 549/469; 556/422; 560/21; 560/52; 560/9; 560/11; 562/435; 562/460
[58] Field of Search .................... 560/21, 52, 9, 11; 562/460, 435; 568/333; 556/422; 549/214

[56] References Cited

U.S. PATENT DOCUMENTS

| | | | |
|---|---|---|---|
| 3,716,586 | 2/1973 | Hofer et al. | 568/333 |
| 3,833,658 | 9/1974 | Binningen et al. | 568/333 |
| 3,898,263 | 8/1975 | Rose et al. | 568/333 |
| 4,024,106 | 5/1977 | Mader | 564/333 |
| 4,577,034 | 3/1986 | Durvasula | 568/333 |
| 4,600,798 | 7/1986 | Cella | 568/333 |
| 4,612,400 | 9/1986 | Durvasula | 568/333 |
| 4,820,791 | 4/1989 | Hergenrother et al. | 528/125 |

OTHER PUBLICATIONS

CA 70(26):116221x, 1969.
CA 113(20):181404e, 1988.
CA 113(26):241491t, 1988.
CA 88(09):62450x, 1978.

Primary Examiner—Jose G. Dees
Attorney, Agent, or Firm—Richard J. Hammond

[57] ABSTRACT

Substituted benzophenones are disclosed having the following formula

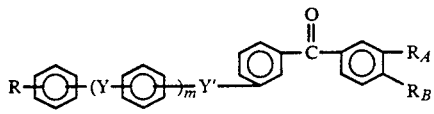

where $R_A$ and $R_B$ are each independently COOH, $C_1$ to $C_{12}$ linear or branched alkyl or taken together to form an anhydride ring, R is nitro or amino unsubstituted or substituted with at least one $C_1$ to $C_6$ linear or branched alkyl, phenyl or substituted phenyl, the substituents being one or more $C_1$ to $C_6$ linear or branched alkyl or $C_6$ to $C_{10}$ aryl, Y and Y' are the same or different and are a chemical bond

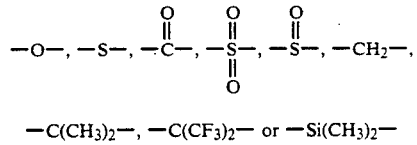

$-C(CH_3)_2-$, $-C(CF_3)_2-$ or $-Si(CH_3)_2-$ and m is 0 or 1 with the proviso that both $R_A$ and $R_B$ can not be hydrogen.

Processes to produce these benzophenones are also disclosed.

10 Claims, No Drawings

SUBSTITUTED BENZOPHENONE DICARBOXYLIC ACIDS

The present invention relates to aromatic ketones and methods for preparing such ketones. More particularly, this invention relates to substituted benzophenones, and the dicarboxylic acids, acid esters and acid anhydrides thereof as well as methods of their preparation.

Linear aromatic or heterocyclic condensation-type polyimides have been an item of commerce for over two decades. The polymer systems that have shown the most success are those that utilize the reaction product of an aromatic dianhydride and aromatic diamine. Because of the difficulty in shaping, coating or other processing of the polyimides produced from the above starting materials, it has been found more convenient to first form a solution of a polyamic acid intermediate, and then to thermally or chemically imidize this intermediate. It has further been found that the control of the physical properties e.g. viscosity of the intermediate can be more easily effected if an end-capping agent is added to the reaction system. These end-capping agents are typically those that carboxylate the terminal amino groups of the developing polyamic acids, advantageously resulting in compositions of high solids but lowered viscosity. Typical end-capping materials are aromatic anhydrides such as phthalic anhydride, naphthalic anhydride and the like. While these agents are effective end-capping materials they do little to effect the physical properties of the final polyimides formed using them. As such, the polymers remain difficult to coat, shape and further process.

It would be advantageous to have an end-capping agent that because of its stereochemistry would effect the physical properties of polyimides prepared from it.

Compositions of matter have now been discovered that can be used as end-capping agents or chain extenders for the preparation of more easily processable polyimides. These compositions are substituted benzophenones dicarboxylic acids, acid esters and anhydrides thereof.

The benzophenone patent and end-capping agents of the present invention are those unsymmetric compounds having the formula

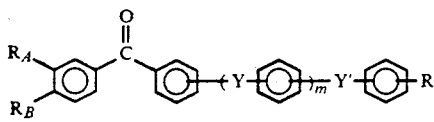

where R is nitro or amino unsubstituted or substituted with at least one $C_1$ to $C_6$ linear or branched alkyl, phenyl or substituted phenyl, the substituents being one or more $C_1$ to $C_6$ linear or branched alkyl or $C_6$ to $C_{10}$ aryl, $R_A$ is the same or different than $R_B$ and individually are hydrogen, —COOH, —COOR$_1$, or taken together form an anhydride ring, where $R_1$ is $C_1$ to $C_{12}$ linear or branched alkyl with the proviso that both $R_A$ and $R_B$ can not be hydrogen, Y and Y' are the same or different and are a chemical bond,

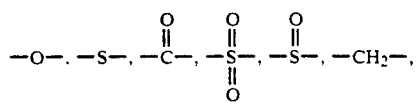

-continued
—C(CH$_3$)$_2$—, —CF$_2$, —C(CF$_3$)$_2$— or —Si(CH$_3$)$_2$—, and m is 0 or 1 e.g., the compounds

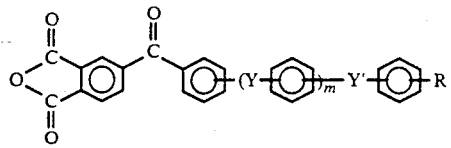

In the above compounds of formula II, the group R is nitro or amino unsubstituted or substituted with at least one $C_1$ to $C_6$ linear or branched alkyl, phenyl, or substituted phenyl the substituents being one or more $C_1$ to $C_6$ linear or branched alkyl or $C_6$ to $C_{10}$ aryl group and Y, Y' and m are as defined above.

In the compounds of formula I, it is preferred that $R_A$ and $R_B$ are the same and are the group carboxylic acid (i.e. —COOH) or the ester thereof, or the anhydrides illustrated by the compounds of formula II. Thus, those preferred compounds of formula I can be the free dicarboxylic acids i.e., $R_A=R_B=$—COOH or their esters, i.e., $R_A$ and $R_B$ are —COOR$_1$ where $R_1$ is $C_1$ to $C_6$ alkyl. Typical esters are the methyl, ethyl, n-propyl, n-butyl, n-pentyl, n-hexyl esters.

In the above preferred compounds preferably m is 0 and Y' is a chemical bond,

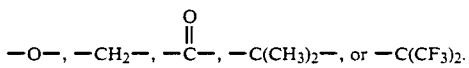

In the compounds of the present invention R is preferably amino or where substituted, the substituent on the amino group are preferably at least one $C_1$ to $C_3$ linear or branched alkyl, phenyl, or substituted phenyl, the substituents being one or more $C_1$ to $C_6$ linear or branched alkyl or $C_6$ to $C_{10}$ aryl (phenyl, naphthyl, etc.).

The most preferable of the compounds of the present invention are those of formula I where $R_A$ and $R_B$ are taken together to form the anhydride ring, m is 0 and Y' is —O—.

The compounds of the present invention where R is amino or substituted amino are prepared by the facile reduction of the corresponding nitro precursors (to the free amine group). A variety of reducing agents can be used to carry out such reduction, i.e., Pd on carbon, lithium aluminum hydride, Raney nickel, etc. with the resulting amine being easily derivatized by further reaction with , for example, alkyl halides (i.e. methyl or ethyl bromide) to form N-alkylamino derivitives or similar reactions with aromatic halides to give the N-arylamino groups.

Illustrative of the compounds of the present invention are the following:
benzophenone-4-(4"-nitrophenyl)-3',4'-dicarboxylic acid;
benzophenone-4-(4"-nitrophenyl)-3',4'-dicarboxylic acid dimethyl ester;
benzophenone-4-(4"-nitrophenyl)-3',4'-dicarboxylic acid diethyl ester;
benzophenone-4-(4"-aminophenyl)-3',4'-dicarboxylic acid;
benzophenone-4-(4"(N-methylaminophenyl)-3',4'-dicarboxylic acid dimethyl ester;

benzophenone-4-(4"(N-dimethylaminophenyl)-3',4'-dicarboxylic acid diethyl ester;

benzophenone-N-phenylaminophenyl-3,'4,'-dicarboxylic acid anhydride;

benzophenone-2-(4"-nitrophenyl)-3',4'-dicarboxylic acid;

benzophenone-2-(4"-nitrophenyl)-3',4'-dicarboxylic acid dimethyl ester;

benzophenone-2-(4"-nitrophenyl)-3',4'-dicarboxylic acid diethyl ester;

benzophenone-2-(4"-aminophenyl)-3',4'-dicarboxylic acid;

benzophenone-2-(4"(N-methylaminophenyl)-3',4'-dicarboxylic acid dimethyl ester;

benzophenone-2-(4"(N-dimethylaminophenyl)-3',4'-dicarboxylic acid diethyl ester;

benzophenone-N-phenylaminophenyl-3,'4,'-dicarboxylic acid anhydride;

As noted earlier the compounds of the present invention are readily prepared by the well known Friedel Crafts acylation procedure, i.e.,

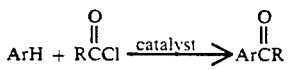

where Ar is an aromatic nucleus and R is aryl or alkyl such as the group

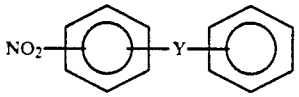

where Y is as previously defined.

In such reaction, catalysts are typically of the Lewis or Bronsted acid type, such illustrated by ferric chloride, aluminum chloride, boron trifluoride, etc. However, in the preferred embodiment of the present invention triflic acid (trifluoromethanesulfonic acid, $CF_3SO_3H$) or similar sulfonic acids have proven to be especially active acylation catalysts. Thus acids known in the art as Super acids such including fluorosulfonic acid, Magic Acid (hydrofluoric acid and antimony pentafluoride) as well as other halo fluoromethanesulfonic acids are useful in causing the reaction to prepare the compounds of the present invention. The following reaction path is illustrative of the preferred method of preparation of the compounds of the present invention

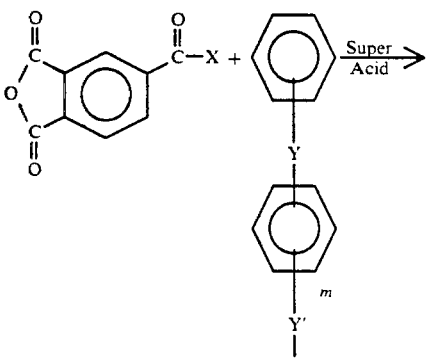

-continued

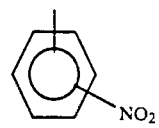

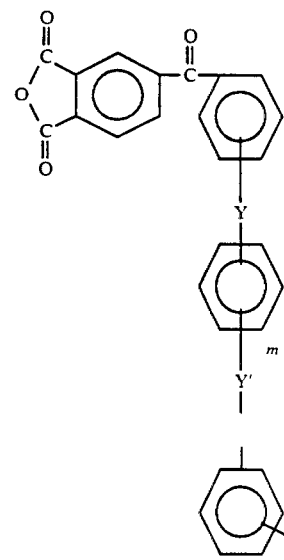

Because these superacids are exceptionally active in causing the acylation to occur as shown above, the general requirement of having a 1:1 mole ratio of acyl halide to Lewis Acid does not apply. See for example U.S. Pat. No. 4,802,791 incorporated herein by reference. Thus, surprisingly small amounts of super acid are effective in causing the acylation reaction. From about 0.1% by weight to about 50% by weight of super acid based on the amount of acyl halide will catalyze this reaction. Depending on the reactivity of the aromatic hydrocarbon (i.e.) methyl substituted are more reactive than unsubstituted ones; smaller amounts of triflic acid can be used (<0.1% preferred).

It should be noted that difunctional aromatic acyl halides of the formula

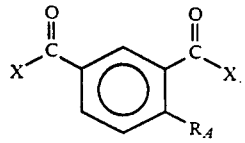

where X, Y and $R_A$ are as previously defined can be controllably reacted with the same or a similar nitroaromatic compound to form compounds of the formula

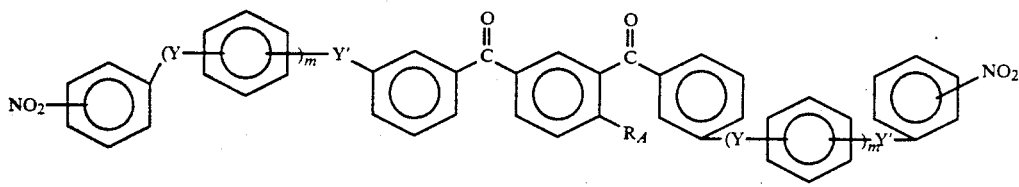

where m and Y' are as previously defined, using the same conditions employed for the mono acyl halide. Reduction of the above dinitro compounds will, of course, produce the diamino derivative. Compounds of this type are useful in the preparation of polyimides or polyamides by reaction with dianhydrides or diacids (or diacid chlorides) as is well known. See for example the relevant chapter in Encyclopedia of Polymer Science Technology, Mark et al editors, Interscience Publishers, -incorporated herein by reference.

As discussed earlier, concerning the amount of $CF_3SO_3H$ necessary to affect the conversion, activated aromatics require lower temperatures than do the deactivated ones. Thus, from about 0.1% by weight to about 50% by weight of super acid based on the amount of acyl halide is preferred to catalyze the reaction.

As indicated from the reaction path shown above, the initial reaction to form the compounds of the present invention is a modification of the Friedel Crafts acylation reaction utilizing an anhydride-substituted aromatic acid halide. The product of the reaction is anhydride-substituted benzophenone compound of formula II. These compounds can be readily transformed into the compounds of formula I where $R_A$ and $R_B$ are the same or different and are $C_1$ to $C_{12}$ linear or branched alkyl esters by an alcoholysis reaction, i.e., reaction of the anhydride with an aliphatic alcohol. While the reaction is typically catalyzed by acids e.g., $H_2SO_4$, Lewis Acids or bases, the preferred catalyst is pyridine or a dilute alcoholic solution of an alkali metal hydroxide.

Similarly, rather than alcoholysis, the compounds of formula I can be converted to the dicarboxylic acids (where $R_A$ and $R_B$ are both the group —COOH) by simple hydrolysis e.g., reaction with water. Such reaction may be conducted with or without a catalyst e.g., an organic or inorganic base.

The alcoholysis reaction and the hydrolysis reaction of the anhydride of the compounds of formula I are well known in the prior art. See for example, the text by March, Advanced Organic Chemistry, McGraw-Hill, New York, N.Y.

Oxidation of compounds of Formula 1 where $R_A$ and $R_B$ are alkyl ester carboxylate groups can be expected to lead to benzophenonetetracarboxylic acids, monomers that are useful in polyimide preparations.

In order for those skilled in the art to be better able to practice the present invention, the following are given by way of illustration and are not to be taken as limiting the scope of the invention in any way.

EXAMPLE 1

1. Synthesis of 1,3-bis[(4-nitrophenoxy)-4,-benzoyl]benzene (BNBB).

A mixture of 4-nitrophenyl phenyl ether (5.0 g), isophthaloyl dichloride (2.4 g) and triflic acid (0.02 g) was stirred under nitrogen for 5.5 hours at 198° C. The reaction mixture was taken up in toluene (100 ml) and stirred with 10% caustic for 30 minutes. The pH of the solution was brought to 7 and the organic layer was separated, dried with anhydrous $Na_2SO_4$ and the toluene stripped off. The residue was crystallized from isopropanal, and dried to give 1.8 g of product. NMR and Mass Spectral data were consistent with the structure. Additional 1.2 g of BNBB was recovered from the mother liquor. Total amount of product recovered was 3 g accounting for a 45% overall yield based on the initial amount of isophthaloyl chloride.

EXAMPLE 2

2. Synthesis of 1,3-bis[(4-aminophenoxy)-4'-benzoyl]benzene (BABB).

A 1 g sample of BNBB in 25 ml ethyl acetate was catalytically hydrogenated at room temperature. An initial pressure of 60 psi was maintained for three hours and the reaction continued further overnight. In the end the reaction mixture was filtered and the excess solvent was removed to give a foamy product (0.93 g). The spectral data was consistent with the structure of BABB.

EXAMPLE 3

3. Preparation of Benzophenone-4-(4''-nitrophenoxy)-3', 4'-dicarboxylic acid (BNPA).

A mixture of 4-nitrophenyl phenyl ether (NDPE, 0.5M), trimellitic anhydride chloride (TMC,0.5M) and trifluoromethanesulfonic acid (4% by weight of TMC) was stirred at 150° C. for 3 hours with a $N_2$ sweep to a caustic scrubber. After cooling to 70° C., an aqueous sodium hydroxide solution (1200 ml $H_2O$, 0.53 mole NaOH) was added with constant stirring. While maintaining the temperature at 70° C., the aqueous layer was extracted with toluene (four 300 ml portions). The aqueous layer was cooled to room temperature to yield white product. The product was filtered, rinsed with water, and dried in vacuum oven to give 103.4 g of off-white solid. This solid was recrystallized from water to yield 94.1 g (Solid A). Based on spectral and wet analysis data, Solid A was determined to be the mono sodium salt of BNPA (Solid A). Five grams of the mono sodium salt of BNPA was stirred in water (45 ml) containing conc. sulfuric acid (2.6 g) for about 24 hours at room temperature. The mixture was filtered, rinsed with water, and vacuum dried at 80° C., to yield 4.6 grams (97%). The structure of this solid was determined as BNPA by a combination of GC/MS, $^1H$ and $^{13}C$ NMR. BNPA was converted to its dimethyl ester and analyzed by mass spec. The exact mass of the dimethyl ester was determined to be 435.092, which corresponded to the formula $C_{23}H_{17}NO_8$. $_1$H NMR($d_6$-DMSO):7.22–7.38 (2 doublets, 4H), 7.76–7.94 (3 doublets, 4H), 7.96–8.03 (s,1H), 8.19–8.33 (d,2H). The total acid titration value was 4.707 meq/g for an estimated purity of 96%. The major product of the above reaction was thus determined to be benzophenone-4-(4"-nitrophenoxy)-3',4'-dicarboxylic acid.

EXAMPLE 4

4. Preparation of benzophenone-4-(4"-aminophenoxy)-3', 4'-dicarboxylic acid(BAPA).

Solid A (20.0 g) was dissolved in 1% caustic solution (2 g of NaOH in 200 ml water) and hydrogenated (65 psi initial H$_2$ pressure) at room temperature in the presence of 1 g of 10% Pd/C catalyst for 20 hours. At the end of the reaction, an additional 0.2 g of NaOH was added to solubilize the solid formed during hydrogenation. The solution was filtered to remove the catalyst and neutralized with glacial acetic acid to form a fluffy white precipitate. The precipitate was cooled in an ice bath, filtered, rinsed with cold water, and vacuum dried at 40° C. to yield 15.4 g of off-white solid. A second hydrogenation was carried out by a similar procedure to generate 15.3 g of product. The combined products (30.7 g) from the two runs were digested at about 70° C. in a 80:20 mixture of isopropyl alcohol/water. This mixture was cooled to room temperature, stirred for several hours and filtered. The product was dried at 40° C. in a vacuum oven to yield 23.7 g product which was identified as BAPA. The structure of this solid was confirmed by $^1$H and $^{13}$C. $^1$H NMR (d$_6$-DMSO):6.51–6.71 (d,2H), 6.76–6.91 (d,2H), 6.91–7.09 (d,2H), 7.66–7.79 (d,2H), 7.79–7.90 (s,2H), and 7.94–8.07 (s,1H). The total acid titration value was 4.941 meq/g for an estimated purity of 93%.

I claim:

1. Compounds of the formula

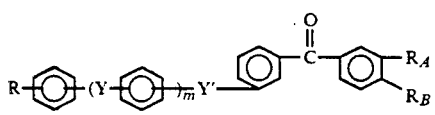

where R is nitro; Y and Y' are the same or different and are a chemical bond,

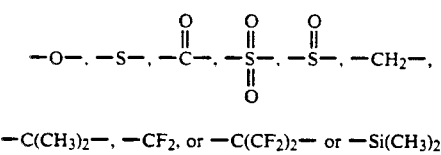

—C(CH$_3$)$_2$—, —CF$_2$, or —C(CF$_2$)$_2$— or —Si(CH$_3$)$_2$—

COOR$_1$, where R$_1$ is and R$_A$ and R$_B$ are each independently hydrogen, —COOH, C$_1$ to C$_6$ linear or branched alkyl or taken together form an anhydride ring with the proviso that both R$_A$ and R$_B$ can not be hydrogen and m is 0 or 1.

2. The compounds of claim 1 wherein m is 0 and Y is a chemical bond,

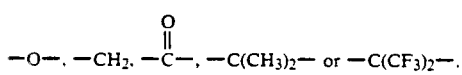

3. The compounds of claim 2 wherein Y' is —O—.

4. The compounds of claim 2 wherein R$_A$ and R$_B$ are each COOH.

5. A process for producing compounds of the formula

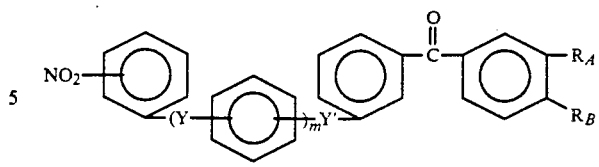

where R$_A$ and R$_B$ are each independently hydrogen, COOH, COOR, or taken together form an anhydride ring where R is C$_1$ to C$_{12}$ linear or branched alkyl with the proviso that both R$_A$ and R$_B$ can not be hydrogen, Y and Y' are the same or different and are a chemical bond,

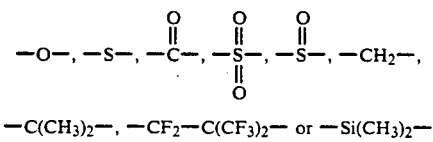

—C(CH$_3$)$_2$—, —CF$_2$—C(CF$_3$)$_2$— or —Si(CH$_3$)$_2$— and m is 0 or 1; comprising treating a compound of the formula

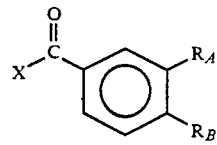

where X is halo and R$_A$ and R$_B$ are as previously described, with a compound of the formula

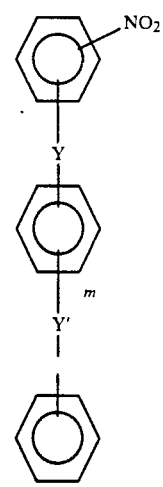

where m, and Y' are as previously defined in the presence of a catalytically effective amount of a Bronstead acid or a Lewis acid catalyst.

6. The process according to claim 5 wherein the catalyst is a super acid.

7. The process according to claim 5 wherein R$_A$ and R$_B$ taken together form an anhydride ring.

8. The process according to claim 7 wherein m is 0 and Y is a chemical bond,

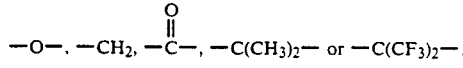

9. The process according to claim 8 wherein Y is —O—.

10. The process according to claim 9 wherein the catalyst is trifluoromethanesulfonic acid.

* * * * *